United States Patent
Kuo et al.

(10) Patent No.: US 9,022,781 B2
(45) Date of Patent: May 5, 2015

(54) ORTHODONTIC APPLIANCES THAT ACCOMMODATE INCREMENTAL AND CONTINUOUS TOOTH MOVEMENT, SYSTEMS AND METHODS

(71) Applicants: Eric Kuo, San Jose, CA (US); Rick Matty, Scotts Valley, CA (US); Artem Borovinskih, San Jose, CA (US)

(72) Inventors: Eric Kuo, San Jose, CA (US); Rick Matty, Scotts Valley, CA (US); Artem Borovinskih, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 13/692,891

(22) Filed: Dec. 3, 2012

(65) Prior Publication Data

US 2013/0209952 A1 Aug. 15, 2013

Related U.S. Application Data

(60) Provisional application No. 61/599,337, filed on Feb. 15, 2012.

(51) Int. Cl.
*A61C 7/12* (2006.01)
*A61C 7/08* (2006.01)
*A61C 7/00* (2006.01)

(52) U.S. Cl.
CPC ... *A61C 7/12* (2013.01); *A61C 7/08* (2013.01); *A61C 7/002* (2013.01)

(58) Field of Classification Search
USPC .................................................. 433/6, 22, 24
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los ngeles, CA, p. 195.

(Continued)

*Primary Examiner* — Ralph Lewis
(74) *Attorney, Agent, or Firm* — Wilson Sonsini Goodrich & Rosati

(57) ABSTRACT

An orthodontic appliance including a shell aligner having a portion accommodating movement of a patient's bracketed teeth between a first position and the second position as elicited by force from an orthodontic braces appliance worn by the patient, related systems and methods.

28 Claims, 11 Drawing Sheets

(56) References Cited

U.S. PATENT DOCUMENTS

| | | | |
|---|---|---|---|
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,559,013 A * | 12/1985 | Amstutz et al. | 433/22 |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,934,288 A | 8/1999 | Avila et al. | |
| 5,954,500 A * | 9/1999 | Spriggs | 433/6 |
| 5,957,686 A | 9/1999 | Anthony | |
| 5,964,587 A | 10/1999 | Sato | |
| 5,971,754 A | 10/1999 | Sondhi et al. | |
| 5,975,893 A * | 11/1999 | Chishti et al. | 433/6 |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,126,443 A * | 10/2000 | Burgio | 433/215 |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,450,807 B1 | 9/2002 | Chishti et al. | |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 8,075,309 B2 * | 12/2011 | Li et al. | 433/80 |
| 8,152,521 B2 * | 4/2012 | Yamamoto et al. | 433/24 |
| 8,292,617 B2 * | 10/2012 | Brandt et al. | 433/6 |
| 8,308,478 B2 * | 11/2012 | Primus et al. | 433/24 |
| 8,539,955 B2 * | 9/2013 | Foster | 128/861 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |

(56) References Cited

U.S. PATENT DOCUMENTS

| | | | | |
|---|---|---|---|---|
| 2006/0078840 | A1* | 4/2006 | Robson | 433/6 |
| 2008/0090196 | A1* | 4/2008 | Lomas | 433/6 |
| 2013/0029283 | A1* | 1/2013 | Matty | 433/3 |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et al, "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004,URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986).
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.

(56) References Cited

OTHER PUBLICATIONS

Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000.
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988.
Duret et al., "CAD/CAM Imaging in Dentistry," Curr. Opin. Dent., 1:150-154 (1991.
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979.
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987.
Friede et al., "Accuracy of Cephalometric Prediction in Orthognathic Surgery," Abstract of Papers, J. Dent. Res., 70:754-760 (1987.
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001.
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982.
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989.
Heaven et a/., "Computer-Based Image Analysis of Artificial Root Surface Caries," Abstracts of Papers, J. Dent. Res., 70:528 (Apr. 17-21, 1991.
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingamp-production/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.
Hoffmann, et al., "Role of Cephalometry for Planning of Jaw Orthopedics and Jaw Surgery Procedures," 0 (Article Summary in English, article in German), lnformatbnen, pp. 375-396 (Mar. 1991.
Hojjatie et al., "Three-Dimensional Finite Element Analysis of Glass-Ceramic Dental Crowns," J. Biomech., 23(11):1157-1166 (1990.
Huckins, "CAD-CAM Generated Mandibular Model Prototype from MRI Data," AAOMS, p. 96 (1999.
Important Tip About Wearing the Red White & Blue Active Clear Retainer System, Allesee Orthodontic Appliances—Pro Lab, 1 page 1998).
Inside the ADA, JADA, 118:286-294 (Mar. 1989).
JCO Interviews, Craig Andreiko , DDS, MS on the Elan and Orthos Systems, JCO, pp. 459-468 (Aug. 1994.
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988.
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46. Jan. 1978.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, KN Am. J. Orthod. Oral Surg. (1946) 32:285-293.
Ki Kamada et.al., Case Reports on Tooth Positioners Using LTV Vinyl Silicone Rubber, J. Nihon University School of Dentistry (1984) 26(1): 11-29.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989.
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989.
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).

(56) References Cited

OTHER PUBLICATIONS

Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and q Essix Appliances, <httpz;//www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et a/., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992.
Rekow, "CAD/CAM in Dentistry: A Historical Perspective and View of the Future," J. Can. Dent. Assoc., 58(4):283, 287-288 (Apr. 1992.
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).

Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992.
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile!Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van der Linden et al., "Three-Dimensional Analysis of Dental Casts by Means of the Optocom," J. Dent. Res., p. 1100 (Jul.-Aug. 1972).
Van der Linden, "A New Method to Determine Tooth Positions and Dental Arch Dimensions," J. Dent. Res., 51(4):1104 (Jul.-Aug. 1972).
Van der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998.
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987.
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization

(56) References Cited

OTHER PUBLICATIONS

'98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (2002).

* cited by examiner

ORTHODONTIC APPLIANCES THAT ACCOMMODATE INCREMENTAL AND CONTINUOUS TOOTH MOVEMENT, SYSTEMS AND METHODS

CROSS-REFERENCE

This application claims the benefit of U.S. Provisional Application No. 61/599,337 filed Feb. 15, 2012, which application is incorporated herein by reference.

BACKGROUND OF THE INVENTION

The present invention relates generally to the field of orthodontics, and more particularly, to dental positioning aligners or appliances accommodating incremental tooth movements as well as continuous tooth movements with braces (e.g., bracket and wire orthodontics), as well as related methods and systems.

An objective of orthodontics is to move a patient's teeth to positions where function and/or aesthetics are optimized. Traditionally, dental devices such as braces are applied to a patient's teeth by a treating practitioner and the set of braces exerts continual force on the teeth and gradually moves them toward their intended positions. Over time and with a series of clinical visits and adjustments to the braces by the practitioner, the teeth reach their final destination and the appliances are removed. These brackets are affixed to the teeth with a bonding adhesive connecting the base of the bracket to the surface of the teeth.

Alternatives to conventional orthodontic treatment with traditional affixed appliances (e.g., braces) are now available. For example, systems including a series of preformed appliances/aligners have become commercially available from Align Technology, Inc., San Jose, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the URL "invisalign.com"). The Invisalign® System includes designing and/or fabricating multiple, and sometimes all, of the aligners to be worn by the patient before the aligners are delivered to the patient and used to reposition the teeth (i.e., prior to the onset of treatment). Often, designing and planning a customized treatment for a patient makes use of computer-based 3-dimensional planning/design tools, such as proprietary Treat™ and ToothShaper™ developed and used by Align Technology, Inc. Aligner design can be based on computer modeling of a series of planned successive tooth arrangements, and the individual aligners are designed to be worn over the teeth and elastically reposition the teeth to each of the planned tooth arrangements.

While recently developed orthodontic treatment technologies such as those described above represent a considerable advancement in the field of orthodontics, additional advancements remain of interest. Even though Invisalign® aligners can be used for a wide range of orthodontic treatment, in some instances orthodontic treatment making use of a combination of both traditional affixed (e.g., bracket/wire) appliances and shell-type aligners may be desired by a treating professional based on the individual needs/desires of the patient. As such, there is a need for innovative products that provide an orthodontic patient with treatment which includes both traditional affixed (e.g., bracket/wire) appliances and shell-type aligners.

BRIEF SUMMARY OF THE INVENTION

The present invention includes structures and related methods providing a combined use of both traditional bracket/wire devices and shell-type appliances or aligners.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
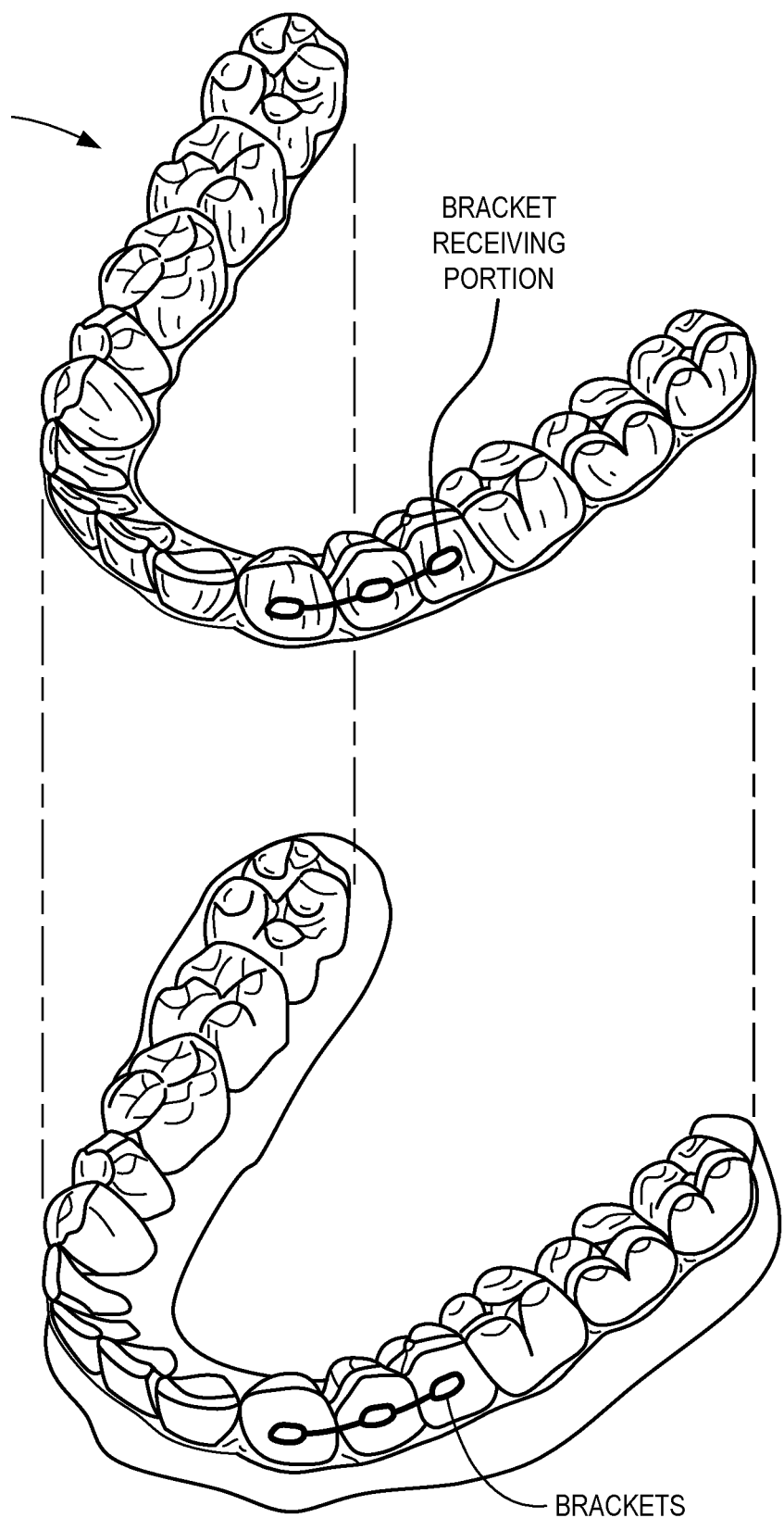
FIG. 1 illustrates an appliance including a braces relief portion and a corresponding jaw of a patient, according to an embodiment of the present invention.

The present invention includes structures and related methods providing combination or dual treatments that use both traditional bracket and wire orthodontics/braces, as well as more newly-developed shell-type appliances or aligners.

A discussion of shell-type appliances or aligners provides an appropriate starting point in a discussion of the present invention with respect to tooth repositioning appliances designed to accommodate a wire and bracket system for a combined shell appliance and wire/bracket system for repositioning teeth. A tooth repositioning shell-type appliance can be worn by a patient in order to achieve an incremental repositioning of individual teeth in the jaw. The appliance can include a shell (e.g., polymeric shell) having teeth-receiving cavities that receive and resiliently reposition the teeth. In one embodiment, a polymeric appliance can be formed from a known thin sheet of suitable elastomeric polymeric material, such a 0.03 inch thermoformable dental material by Tru-Tain Plastics, Rochester, Minn. An appliance can fit over all teeth present in an upper or lower arch, or over less than all of the teeth. In some cases, only certain teeth received by an appliance will be repositioned by the appliance (e.g., certain teeth covered by the appliance will receive orthodontic forces) while other teeth can provide a support or anchor region for holding the appliance in place as the other portions of the appliance apply force against the tooth or teeth targeted for repositioning. In some cases, many or most, and even all, of the teeth will be repositioned at some point during treatment depending on the aligner configuration at the time. Teeth that are moved at one point during treatment (e.g., moved teeth) can also serve as a support or anchor for holding the appliance and vice versa, throughout the course of the appliances being worn by the patient. In a series of appliances, some appliances may engage the teeth without the need for supplemental assistance for appliance retention, but in some cases, it may be desirable or necessary to provide individual anchors bonded on the teeth with corresponding receptacles or pockets in the appliance so that the appliance can apply a specific force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the URL "www-.invisalign.com").

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where dental surgery is prescribed (e.g. tooth extractions), where interproximal reduction (IPR) or tooth reshaping for the creation of space is needed, when a progress check is needed, where spaces are needed for post-orthodontic dental restorations, where anchor placement on the tooth surface is optimal, where the aligner trim line should be located, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The aligner appliances can be generated all at the same time or in sets or batches. The patient wears each appliance for a fixed length of time as instructed by their prescribing doctor, typically 20-22 hours a day, and from 10-21 days for each appliance. A plurality of a series of different appliances, with each upper and lower jaw pair being a "set" in the series, can be designed and fabricated prior to the patient wearing any appliance of the series. After wearing an appliance in the set for an appropriate period of time, the patient replaces the current appliance(s) with the next appliance(s) in the series until the appliances in the series have been worn. Additional series of appliances may be fabricated and worn until a satisfactory treatment outcome is achieved. Unlike orthodontic brackets which are directly bonded to the teeth, the aligner appliances can be removed by the patient throughout the treatment process (e.g., during eating, brushing, etc.).

Bonded orthodontic braces move the teeth as a result of orthodontic force (pressure) delivered to the teeth via an orthodontic wire which is connected to the brackets. The wire is elastically deformed when it is tied to the braces, and as the wire tries to return back to its original shape, the teeth which are connected to the wire are pushed or pulled by the wire as it reconfigures itself from the distorted position back to its relaxed position. Sometimes springs or rubber bands are used to put force in a more specific direction. For example, springs placed on an archwire can help push apart or bring together teeth along the archwire. Rubber bands can help coordinate the upper and lower jaw by pulling teeth in one jaw against teeth in the other jaw. Fixed braces tend to apply a more continuous pressure whereas aligners apply incremental or interrupted forces because of their removable nature.

Some embodiments of the present invention includes one or more shell-type aligners or appliances that accommodate braces (brackets and wire(s)) positioned on the patient's teeth to allow for simultaneous treatment with braces and shell-type aligners. Such appliances will typically engage certain teeth so as to apply a repositioning force to those teeth, as well as accommodate teeth to have braces (brackets and wire(s)) coupled simultaneously therewith. Systems and methods described herein can include a single aligner or a plurality or series of aligners—e.g., a plurality of aligners designed to be sequentially worn by a patient.

FIG. 1 illustrates an appliance that accommodates braces positioned on the patient's teeth. A jaw of the patient is shown having braces bonded to several teeth. The tooth repositioning appliance can include an appliance as described above and further modified or configured to accommodate the braces positioned on the patient's teeth. The appliance can be worn by the patient in order to achieve incremental positioning of individual teeth in the jaw. The appliance includes a shell having teeth-receiving cavities that receive teeth and apply a resilient force to one or more of the teeth received. The appliance shell further includes a braces or bracket receiving portion that accommodates the positioned braces. Accommodation can be defined as cutouts in the aligner which border around the braces or component thereof (e.g., bracket, wire, etc.), or a covering (partial or full) over the braces or component in such a way that the aligner can be placed and removed without dislodging the brackets. As described further herein, the braces or bracket receiving portion of the appliance will typically include a movement path volume or geometry configured to receive the braces and accommodate a certain range of movement of the bracketed teeth during orthodontic treatment or a particular phase thereof.

As used herein, the term "braces" generally refers to one or more components of a bonded orthodontic braces appliance configured to retain or move teeth as a result of orthodontic force(s) delivered to brackets positioned on the patient's teeth. A braces component can include bracket(s), wire(s), elastic(s), ligature(s) and the like. A relief portion (e.g., braces or bracket relief portion) of an appliance can be configured to accommodate one or more components of an orthodontic braces appliance, e.g., as described further herein. A bracketed tooth, as used herein, refers to a tooth of the patient having a bracket or braces appliance positioned therein. Thus, a bracketed tooth may include a positioned bracket only, or a positioned bracket and one or more additional components of a braces appliance.

One attempt to accommodate bracketed teeth in a shell type aligner may include aligners manually trimmed by the doctor to remove aligner material that might otherwise cover the brackets and/or tooth areas where the brackets and wires are positioned or to be positioned. Problems typically arise with such an approach, however, due to a lack of sufficient coordination between the aligners delivering fixed increments of tooth movement, and the braces delivering continuous, undefined movements. As a result, a problem of aligner fit can become an issue as a result of the asynchronous coordination between the expected tooth movement built into the aligners and the actual tooth movement accomplished by the braces. In other words, the braces may not move the teeth sufficiently to the next pre-defined increment defined within the aligner shell by the time the patient changes the aligners, or if the braces move the teeth beyond the pre-defined increment by the time of the next aligner change. Such decoupling between the movement elicited by the aligner and the movement elicited by the braces can result in a non-fitting or ineffective shell appliance that no longer works for the patient. Cutting away of aligner material can also weaken the aligner structure, and may minimize or eliminate the desired effect on the tooth/teeth to be moved.

A challenge, therefore, is to create a system that allows for incremental (e.g., pre-programmed aligner-elicited movement) as well as continuous (e.g., braces elicited movement) tooth movements concurrently or simultaneously. One approach is to plan or predict the movements from both system components and design aligners precisely to fit and deliver tooth movement at identified stages or phases of treatment based on known biological tooth movement rates published in the scientific literature. For example, one may try to predict the rate of tooth movement that can be achieved with different bracket and wire systems. Since the rate of tooth movement with braces depends on a number of variables, including but not limited to the type of wire material used (e.g. stainless steel vs. nickel titanium), the size of the wire used (e.g. 0.014 inch, 0.018 inch), the shape of wire used (square vs. round), the age of the patient, the gender of the patient, the size of the tooth root, the bone level around the tooth, the type of bone (maxillary or mandibular; maxillary has better blood circulation), and whether certain medications may be taken prior to and/or during treatment (e.g., anti-inflammatory drugs, bisphosphonates).

Another approach includes identifying a movement scenario that builds into an aligner a space or relief that accommodates a fixed increment of tooth movement with or without a margin for deviation. For example, an aligner may be built so as to accommodate an increment of movement that exceeds the most likely scenario of tooth movement for the braces portion (which could be based on rates published in the scientific literature for example), and including an additional space that allows certain teeth (the bracketed teeth) to freely move from the current positions to the maximum likely tooth movement positions. This prevents the aligners from interfering with the tooth movement and prevents the teeth with the braces from preventing aligner seating. The most extreme version of this approach would be to accommodate the bracketed teeth from the beginning position all the way to the end position. In this extreme scenario however, the aligner portion covering the bracketed teeth may be loose and uncomfortable for the patient, especially if the distance for the tooth to travel is large. Furthermore, an even greater deviation may be needed as an accommodation if the actual path of the tooth requires a non-linear deviation from the beginning to end position. For this reason, and also to accommodate such non-linear paths of teeth and/or different tooth movement timing sequences (e.g., canines being retracted first, then the anterior teeth later), having a limited range of possible movements from the current position is a better alternative than encompassing the entire planned path for each tooth being bracketed.

Figure 2:
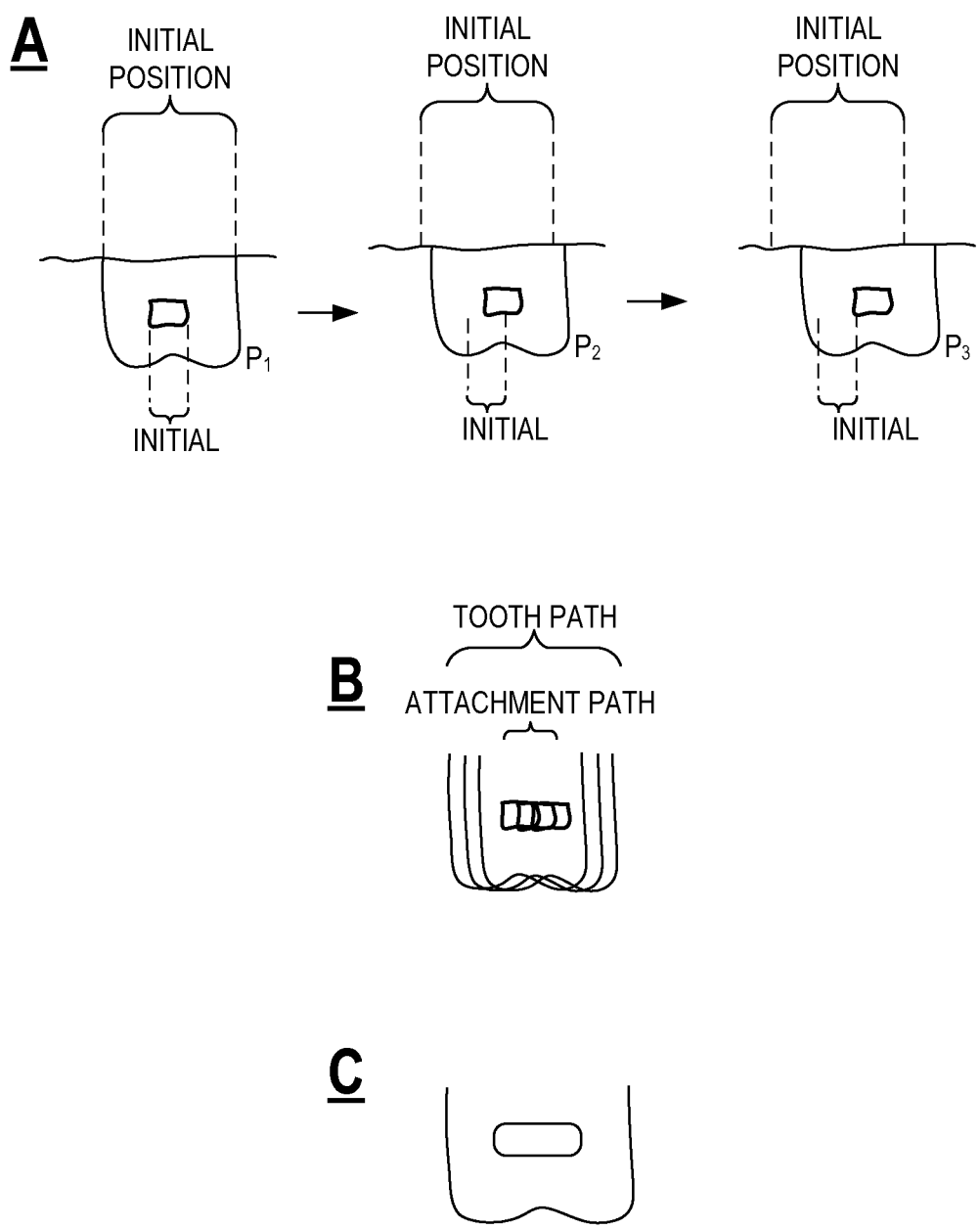
FIG. 2A through 2C illustrate tooth movement between an initial position and subsequent positions (FIG. 2A); tooth and bracket location in illustrated positions; and an aligner relief portion accommodating bracketed tooth movement between illustrated positions.

In one embodiment, the braces portion of the aligner (the part which accommodates the teeth with the braces bonded to them) can include a tooth movement path volume or geometry determined based on identified or predicted movement of a tooth or teeth between two or more positions. Identifying a tooth movement path and the corresponding volume or geometry of a bracketed tooth moving along the path digitally or by computer, and designing a corresponding aligner to accommodate the movement path volume or geometry is illustrated with reference to FIGS. 2A-2C. One or more of various types of tooth movements may be accomplished, including but not limited to, inclination, angulation, translation, rotation, intrusion, extrusion, or combinations thereof and eliciting a tooth movement. The present invention will not be limited to any particular movement or movement type. For illustrative purposes, FIG. 2A diagrams a simplified tooth movement (translation) between positions $P_1$, $P_2$, and $P_3$. FIG. 2A shows a tooth at position $P_1$ with dashed lines providing a reference point for tooth and bracket positioning at the "initial position." As the tooth moves to $P_2$, both the tooth and the bracket are shifted right relative to the initial tooth and bracket positions as in $P_1$. Further movement of the tooth to $P_3$ further shifts tooth and bracket positioning relative to the initial position of the tooth and bracket. FIG. 2B shows tooth and bracket positions at $P_1$ through $P_3$ overlaid to illustrate the movement path volume or geometry (the geometric summation of the incremental tooth movement as the increment of movement approaches zero from initial to target position) of the tooth with its bonded bracket. The movement path may include and be defined by a plurality of staged tooth positions as described, and may further include interpolation of tooth positions between particular identified or digitally represented tooth stages or positions. FIG. 2C illustrates an aligner portion having a movement path volume or geometry based on predicted or computed movement of the tooth and bracket between $P_1$ through $P_3$. The aligner includes a tooth receiving cavity having a volume and geometry shaped to accommodate a path of movement of the tooth between $P_1$ through $P_3$. The aligner further includes a relief portion, e.g., braces-receiving relief portion, having a volume and geometry shaped to accommodate a path of movement of the bracketed tooth between $P_1$ through $P_3$.

Figure 3:
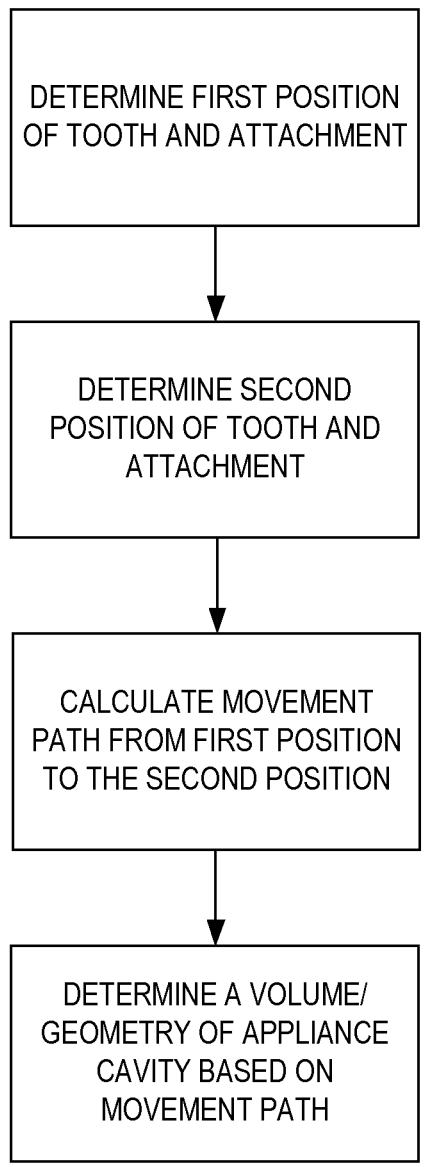
FIG. 3 illustrates a method according to an embodiment of the present invention.

FIG. 3 is a flowchart illustrating steps of a method, such as a computer-implemented method, for providing an aligner accommodating a braces-elicited movement of one or more bracketed teeth. A method includes determining a first position of a bracketed tooth. Next, is a determination of a second position of the bracketed tooth. Thereafter, the movement path from the first position to the second position is determined or calculated. Next, a movement path volume or geometry is determined based on the first and second positions and the movement path of the bracketed tooth. An appliance is designed and/or fabricated including a portion or relief in the appliance cavity configured with a volume or geometry to accommodate movement of the bracketed tooth according to the calculated movement.

Figure 4:
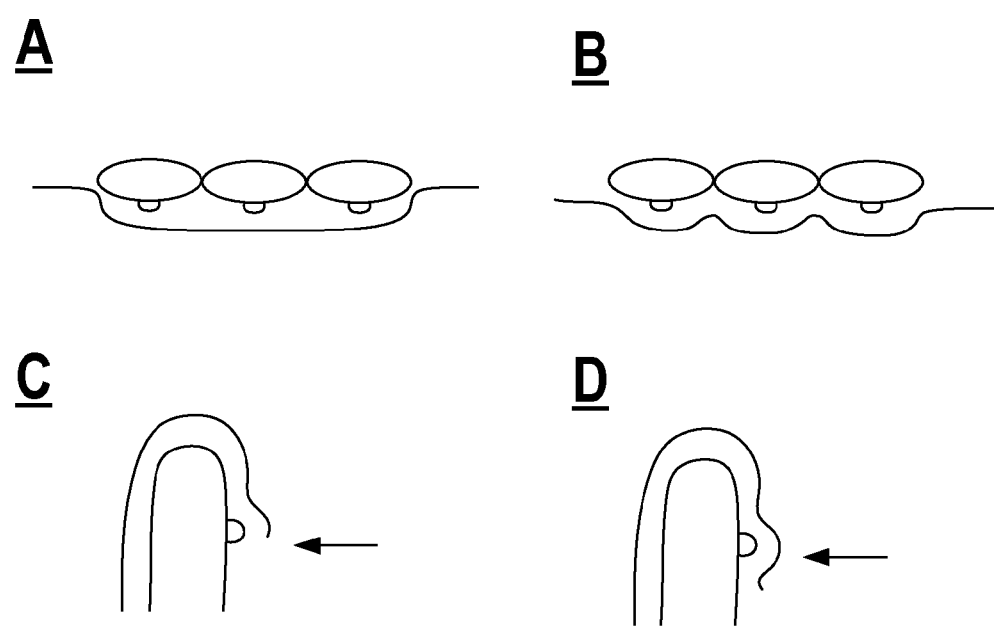
FIGS. 4A through 4D illustrate aligners including a tooth receiving cavity and braces relief portion according to embodiments of the present invention.

As discussed above, various aligner shapes and/or designs can be selected for use in a combined aligner and braces system as described herein, and aligners will not necessarily be limited to any particular shape, geometry or design. As discussed above, an aligner can include a receiving portion or relief shaped to accommodate positioned bracket or braces. Various suitable shapes and/or designs can be accomplished according to the systems and methods described herein. Certain non-limiting examples of aligner shapes or designs are provided with reference to FIGS. 4A through 4D. FIG. 4A shows a cross-section view of an example aligner portion shaped to accommodate braces/bracketed teeth, where the aligner wall extends outward laterally from the bracketed tooth surfaces to form a relief portion. FIG. 4B is another example of an aligner portion shaped to accommodate braces/bracketed teeth, where the aligner wall extends outward to form a non-uniformly shaped relief portion.

An aligner or relief portion thereof can be shaped or designed to facilitate placement of the aligner on the patient's teeth (bracketed teeth), while minimizing unwanted contact between the aligner and braces. For example, the aligner relief portion may be shaped to minimize contact between the aligner and braces that might make placement of the aligner over teeth difficult or potentially damaging to the aligner and/or braces structure. FIG. 4C shows a cross-section side view of an aligner positioned over a tooth having a bracket attached. The side of the aligner extending over the bracket has a shortened side wall that extends less than the entire distance of the tooth crown portion, or less than the entire distance between the occlusal portion of the tooth and gingival line or edge. FIG. 4D is a side view showing an aligner positioned over a bracketed tooth, where the relief portion having a distal portion or portion extending in a gingival direction and flared laterally so as to minimize an edge of the aligner catching or butting against the bracket during aligner insertion and removal.

The aligner or relief portion thereof can include various shapes or designs, and may include, for example, a protrusion, bubble, envelope, slot shape and the like. The relief portion may be defined by a continuous or substantially continuous portion of the aligner or material, or may be composed at least partially or wholly of one or more materials different from material(s) forming other parts of the aligner. In some instances, a relief portion may form an open portion, so as to form a hole, window, annulus, and the like. A relief portion may include or define an insertion path (e.g., a passive insertion path) to receive the braces/bracketed tooth so the aligner avoids contacting or clipping the attachment structure (e.g., bracket, wire, elastic, elastic chain, springs, etc.). Thus, as discussed further herein, the relief portion can be designed to reduce or minimize unwanted contact that might disrupt or damage the bracket positioned on a tooth, or otherwise disrupting a braces component.

Figure 5:
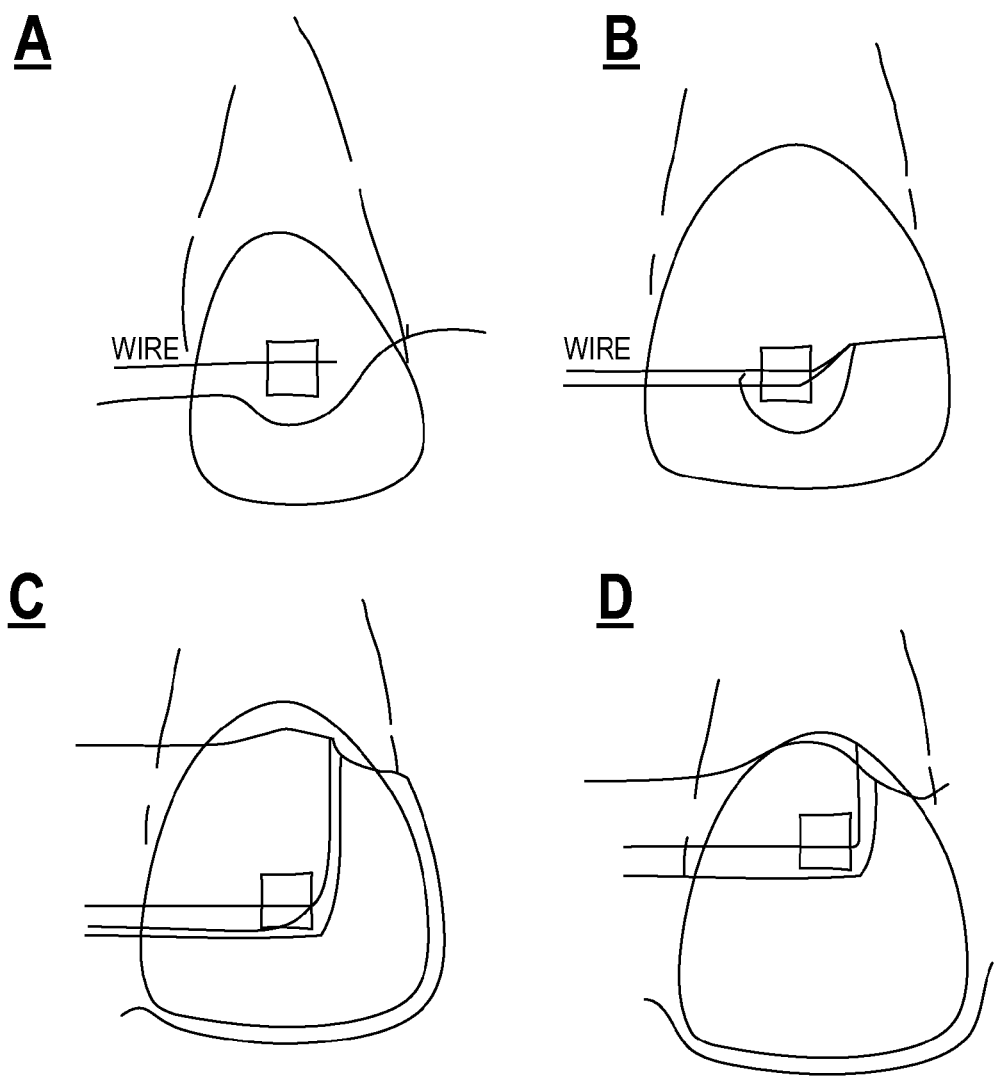
FIGS. 5A through 5D show aligners including a tooth receiving cavity and braces relief portion according to embodiments of the present invention.

Further non-limiting examples of aligner shapes or designs are provided with reference to FIGS. 5A through 5D. Each of the illustrated examples show an aligner having a tooth receiving cavity and a braces relief portion, the cavity and relief having a structure or geometry shaped to accommodate movement of a braces/bracketed tooth along a movement path as described herein. FIG. 5A shows an aligner having a tooth receiving cavity with a relief portion, where the relief portion includes a portion of the aligner that is open to the braces, e.g., forming a cut-out or cut-away, such that the braces are not substantially received within the cavity or relief portion. FIG. 5B shows an aligner having a tooth receiving cavity and a relief portion that at least partially receives the bracket/braces as the aligner is positioned on the patient's teeth. The relief potion forms a bubble or envelope that extends out laterally relative to the adjacent portions of the aligner or adjacent surface of a tooth received in the aligner cavity. As shown, the relief portion is shaped such that the bracket is at least partially disposed within the relief portion, and the wire remains at least partially outside the relief portion. FIG. 5C shows an aligner having a tooth receiving cavity and a relief portion, where the relief portion defines an envelope or channel shaped to accommodate a received bracket and wire. The envelope extends both laterally and vertically (i.e., along a long axis of the tooth). The envelope can include a portion that extends or protrudes further outward compared to an adjacent portion of the envelope, so as to more easily receive and accommodate bracket positioning as the aligner is positioned or removed from the patient's teeth. FIG. 5D shows an aligner having a tooth receiving cavity and a relief portion, where the relief portion defines an envelope or channel shaped to accommodate a received bracket and wire positioned more gingivally on the tooth.

Various types of movements and positioning of the teeth may be accommodated according to the methods and techniques described herein. Movement between two or more positions can include initial, intermediate, and/or final position of the teeth per overall treatment or a phase of treatment. In one embodiment, the braces-receiving relief portion of the aligner between an initial position to a target position includes an intermediate position before reaching the final desired goal position. The defined path of the tooth and its bracket do not need to follow a linear path. See, e.g., FIG. 9.

In another embodiment, the braces accommodating or relief portion of an aligner includes a movement path volume or geometry which accommodates a selected range of tooth movement (e.g., maximum possible tooth movement) in a selected increment of time that the aligner is to be worn. For example, if teeth would not be reasonably expected or predicted to move more than 1 mm in one month, than a +1 mm envelope of movement programmed into an aligner that is to be worn for 2 weeks would adequately contain enough space for the teeth with the braces to move freely.

In another embodiment, the braces accommodating or relief portion of an aligner includes a shape, or volume or geometry, which accommodates a selected range of tooth movement, where the range of movement is based on an identified or predicted movement further including a sort of "error margin" or buffer distance for less movement and greater movement than that identified or predicted. For example, the braces portion contains movement ahead as well as behind according to a fixed interval (the increment itself does not necessarily have to be symmetric, meaning the forward increment can be greater than the backward increment or vice versa), to account for the possibility that the teeth with the braces might not be caught up to expected positioning, as well as to account for the possibility that some or all of the bracketed teeth may move more rapidly than expected at any particular stage. In other words, if the teeth are at a position time point T, then the braces portion might be T+X and T−X if the increment of cushion is the same, or T+X and T−Y if the buffer increment are not the same (e.g. a buffer of 4 weeks of anticipated movement forward, and the position of the teeth 2 weeks prior to the anticipated target). A potential advantage of the forward (and "backward")-looking fixed increment of time (or corresponding movement) is that variants in staging pattern such as canine-retraction first and non-simultaneous selective movements can be built into the treatment plan without creating a large bubble in the aligner, which may be the case if the entire path from before to after is built into the sectional region for the braces. By not creating a large bubble, the aligner is better retained to the teeth and the chance of tissue irritation from the cheeks and lips being trapped underneath the aligner is reduced.

In another embodiment, an aligner braces/bracket relief portion may be configured such that certain directions of tooth movement are enabled whereas certain directions are restricted. For example, the vertical position of the teeth (extrusion) may be restricted to prevent the teeth from erupting early in the treatment, whereas the rotations and translations may be unrestricted. This allows certain types of movements to be restrained from taking place for the purpose of better dimensional control and the reduction of undesired side-effects, such as with vertical extrusion of molars for example. An aligner may be configured such that a relief portion accommodates or restricts a particular range of movement within a given direction or movement vector. See, e.g., FIGS. 6 and 7.

An aligner as described herein can be configured such that a target or final position of a tooth accommodated by an aligner's braces/bracket relief portion or section reflects tooth movement or an end point that the braces with the wire will accomplish. In a braces-elicited tooth movement, the tooth position is governed by the position of the braces on the teeth as well as the prescription built into the bracket, which the wire will move the teeth to as the wire straightens out from the initial active "bent" position when the wire is engaged in the brackets to the relaxed or passive position. Therefore, setting up the target position of the teeth with the likely position of the teeth given the prescription of the brackets may be important to the accuracy of the fit of the aligner throughout treatment. During the setup process, a simulation of the actual bracket and intended final wire arch form may be used to establish the goal or target position of the teeth to which brackets will be bonded. Otherwise the wire will move the teeth with the brackets towards a goal programmed into the bracket, but the aligners may try to move the teeth towards a different goal, and this mismatch will either lead to a poor fit of the teeth with the aligner, or the teeth will be constantly jiggled back and forth between the two positions when the aligners are taken on and off, and the braces are free of the aligner constraints while the aligners are not being worn.

The number of brackets positioned on teeth and/or accommodated by an aligner as described herein can vary and is not limited to any particular number of brackets and wires. As the minimum number of brackets that can be connected by a section of arch wire is two brackets in an arch, aligners as described herein will typically accommodate two or more brackets. Brackets can be positioned through various manners, including manually or digitally, and directly or indirectly, using any number of bracket-positioning systems.

A process or mechanism for bonding the brackets can be any number of techniques or technologies, including but not limited to indirect bonding trays where brackets are included (e.g. Cadent iQ), placement jigs (e.g. Insignia, Incognito lingual), and/or bracket placement guides (Align's bracket positioning template). Orthodontic bracket positioning may make use of one or more bracket positioning templates, including templates such as those described, e.g., in U.S. Pat. No. 7,658,610.

Techniques may be employed to ensure that the final position of the teeth built into the aligner is based on the position of the teeth that the bracket will move the teeth to when the wire is fully expressed. For a section or span of teeth (i.e., two or more teeth adjacent to each other), the position of the teeth relative to each other is important, and may be more relevant compared to the absolute position of the section relative to the jaw. This is because the braces section only aligns the teeth with the brackets relative to each other. The entire unit of the sectional fixed appliances will be positioned relative to the teeth being moved by the aligners, based on the orientation of the braces section relative to the non-bracketed section in the aligner.

As will be recognized, aligners as described herein can include various geometries or configurations can be selected or designed for use as disclosed. Aligners can be shaped or designed to accommodate one or more of the following functionalities: retention of tooth/teeth positioning, prevention of a particular movement or movement type of a tooth; enhancement of movement or force applied to a tooth/teeth due to bracket placement and wearing braces (i.e., the aligner can assist in the movement of the bracketed teeth rather than be passive in those regions of the appliance); facilitating guidance of a tooth or teeth along a particular tooth movement path; protection of certain tissues (e.g., tongue, cheeks, lips) from bracket contact or irritation.

For example, in some instances, the doctor may prescribe that movement of one or more teeth is not desired during treatment or during a particular phase of treatment. An aligner of the present invention can be selected or designed such that the corresponding tooth receiving cavity of the aligner is shaped to facilitate retention of the tooth in a particular position in order to maintain the current position of the tooth. One example is where a tooth or teeth are utilized as an anchor position, either bracketed or unbracketed, so as to facilitate the application of a movement force to the other teeth of the patient's dentition. Such an aligner can be shaped to facilitate retention of the anchor tooth/teeth in the desired position during treatment. In another example, a particular tooth or teeth may have been moved at an earlier stage of treatment and it is desired that said teeth be held or maintained in their current positions. An aligner can be shaped or designed to facilitate retention of the tooth in the current or target positioning while additional orthodontic treatment (e.g., further movement) takes place either simultaneously or sequentially (e.g., movement primarily by braces then aligners then braces, or movement primarily by aligners then braces).

In another example, and in furtherance of discussion herein, an aligner can be shaped or designed so as to facilitate prevention of tooth movement in a particular manner and/or to guide tooth movement in a desired direction or path of movement. An aligner or portion thereof designated as a relief portion can be configured such that certain movement vectors or paths (including non-linear ones) of movement are enabled whereas certain movements are restricted. In this manner, aligners can be designed or selected so as to enable better dimensional control or "fine-tuned" movement of teeth with treatment.

Figure 6:
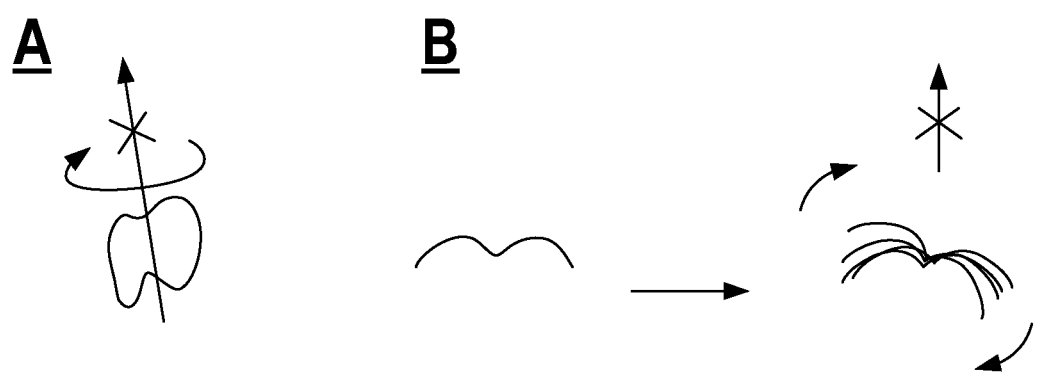
FIGS. 6A and 6B conceptually illustrates building an aligner restricting tooth extrusion but allowing tooth rotation, according to an embodiment of the present invention.
Figure 7:
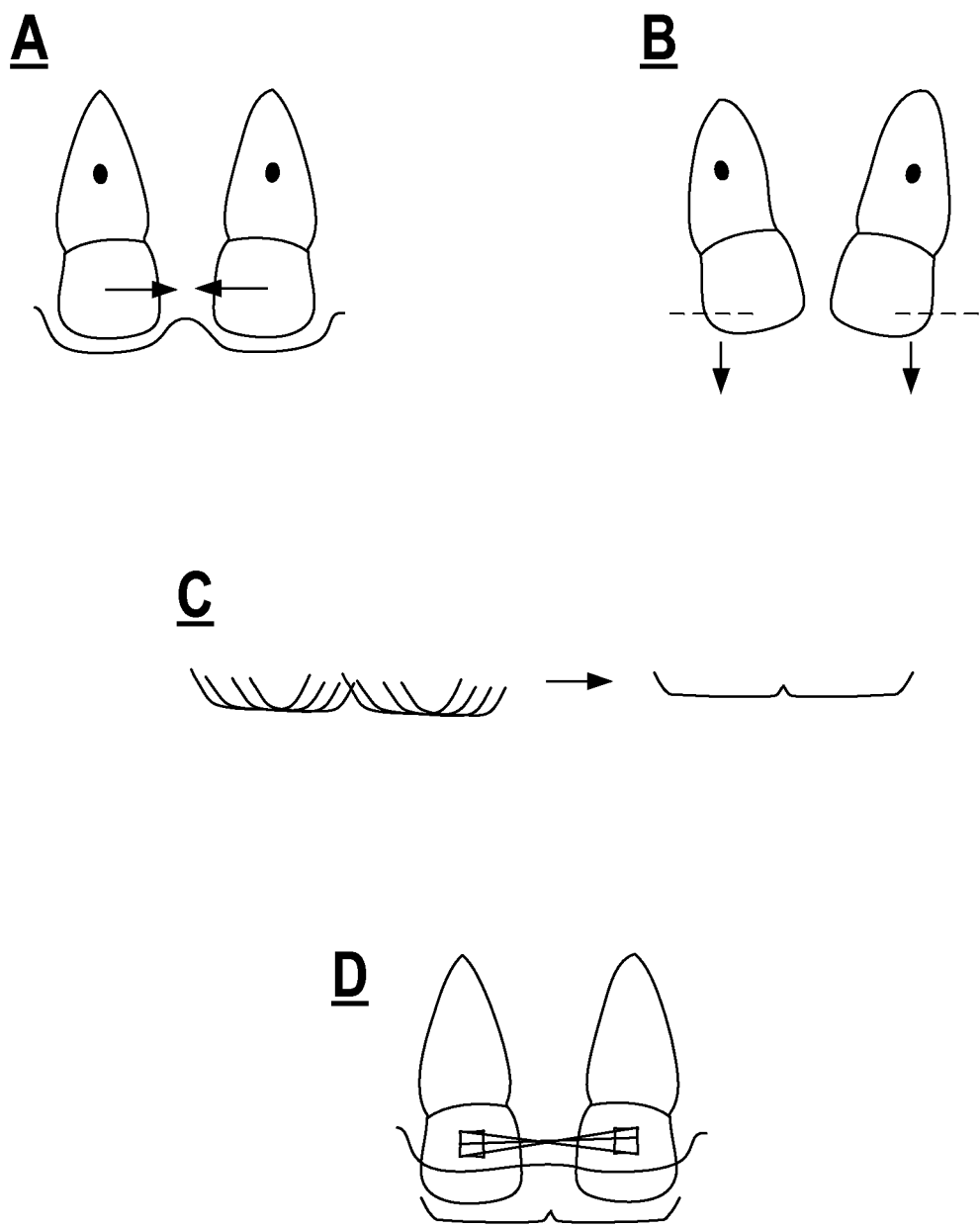
FIGS. 7A through 7D illustrate tooth movement and building an aligner restricting tooth extrusion but allowing tooth translation, according to an embodiment of the present invention.

FIG. 6 illustrates restriction of posterior tooth extrusion but allowing tooth rotation as an example of aligner design where certain movement vectors or paths of movement are enabled whereas certain movements are restricted. FIG. 6A illustrates a tooth where the desired movement is illustrated with the curved arrow showing a desired rotational movement, and a vertical arrow showing the desired restriction of movement along a vertical movement vector or path (e.g., restrict or prevent extrusion movement of the tooth). FIG. 6B shows conceptual design and shaping of an aligner crown portion. A 2D cross-section of a crown portion of a tooth is shown. As the tooth is moved from a first position to subsequent positions to accommodate the rotational movement, corresponding staged 2D cross-sections are superimposed to illustrate a tooth movement path as the tooth rotates. The staged 2D cross-sections define a tooth movement path where tooth rotation is permitted, but lateral extrusion movement of the tooth is restricted or blocked by the crown portion of the aligner cavity. In computer aided design, such movement can be enabled by filtering certain directional vectors in a computer-implemented treatment planning or staging program.

FIG. 7A through 7D illustrates restriction of upper anterior extrusion while allowing for translation, e.g., for space closure, as another example of aligner design where certain movement vectors or paths of movement are enabled whereas certain movements are restricted. FIG. 7A shows teeth received in an aligner where translation movement is desired for space closure. FIG. 7B illustrates undesired anterior extrusion that might result from force application to the tooth crowns without restriction of the vertical movement component. As a force is applied laterally to the tooth, the applied force may elicit tooth translation but also may elicit tipping or rotation around a center of rotation of the tooth with an extrusion or vertical movement component. FIG. 7C shows 2D cross-sections of aligner crown portions for a series of movement stages to illustrate a movement path, and further illustrates removal of intermediate stages such that the aligner crown portion is shaped to accommodate the movement path of the tooth. The crown portion is shaped to allow movement of the teeth along the movement path while restricting vertical movement so as to restrict tooth extrusion. FIG. 7D shows teeth having braces, where the teeth are positioned in an aligner having a cavity shaped to accommodate movement of the teeth along a translation movement path allowing for space closure. As movement forces are applied to the teeth, the aligner cavity accommodates translational movement while restricting tooth extrusion.

Figure 13:
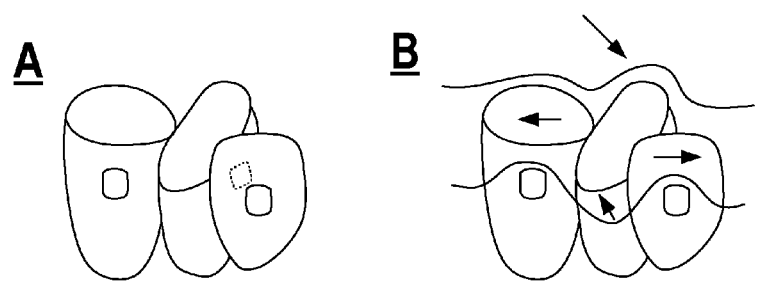
FIGS. 13A and 13B illustrate teeth (FIG. 13A) and teeth and a corresponding aligner (FIG. 13B), according to an embodiment of the present invention.

In yet another embodiment, an aligner or portion thereof can be designed or shaped to work in conjunction with braces-elicited movement such that the movement force(s) applied to the teeth via braces are facilitated or further enhanced. In one example, a movement is elicited to a tooth (or plurality of teeth) that is the net result of action by both an aligner and braces. This may occur where both the aligner and the braces impart movement forces to the tooth, with the system of forces combined to elicit a particular movement to the tooth. In another example, one of the braces or the aligner may contact the tooth and act as a leverage point or point of resistance to the tooth that affects the movement force applied by the other orthodontic component. With such dual use, treatment may be enhanced so as to allow improved movements (e.g., better translation, reduced tipping, etc.) than might be accomplished using braces alone. Treatment time may also be shorter because in some instances, for example, the teeth surfaces may only be accessible for movement to be accomplished by one mechanism (aligners) but not the other (brackets, in the case of severe rotation or deep bite). See, e.g., FIG. 13.

Figure 8:
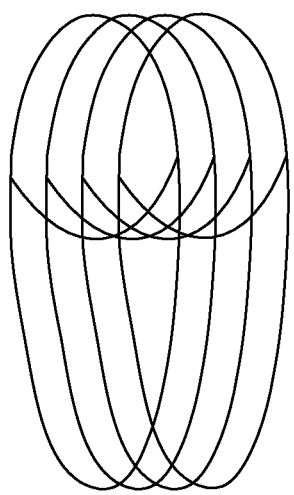
FIGS. 8A and 8B show a staged tooth movement and a corresponding portion of an aligner shaped to accommodate the staged movement and apply force, according to an embodiment of the present invention.
Figure 8:
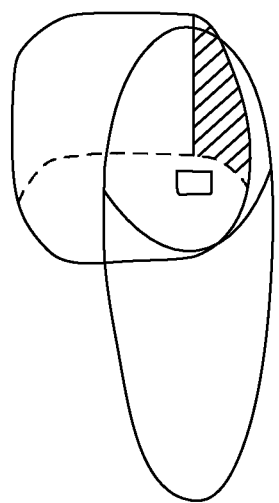

FIGS. 8A and 8B show a staged tooth movement and a corresponding portion of an aligner shaped to accommodate the staged movement and additionally apply a force to the tooth in conduction with worn braces. FIG. 8A shows staged tooth movements between sequential positions (e.g., P1 through P4)—for example, a first position (e.g., start position) and a subsequent position (e.g., target position), with intermediate positions therebetween. FIG. 8B shows an aligner with a cavity portion positioned relative to the tooth in the first position of FIG. 8A. The aligner includes a tooth-receiving cavity portion that is shaped to at least partially accommodate the tooth movement path geometry or volume. The tooth-receiving cavity further includes a relief portion, which may be shaped to accommodate movement of the braces throughout the entire tooth movement, e.g., as shown in FIG. 8A. The aligner cavity portion is shaped so as to apply a resilient force to the tooth during only a portion of the movement path. For example, when the aligner is positioned over the patient's teeth, the aligner may stretch to accommodate the tooth in the first position, thereby applying a resilient force due to elastic deformation of the aligner material. The aligner cavity includes an active portion that contacts the tooth for application of the movement force applied by the aligner. The aligner may be shaped such that the aligner reaches a non-deformed or relaxed state as the tooth reaches an intermediate position but prior to the tooth moving to the target position. Furthermore, the geometry of the tooth receiving cavity may be selected or shaped to guide tooth movement along the defined movement path and/or restrict one or movements or directions of the tooth.

Figure 9:
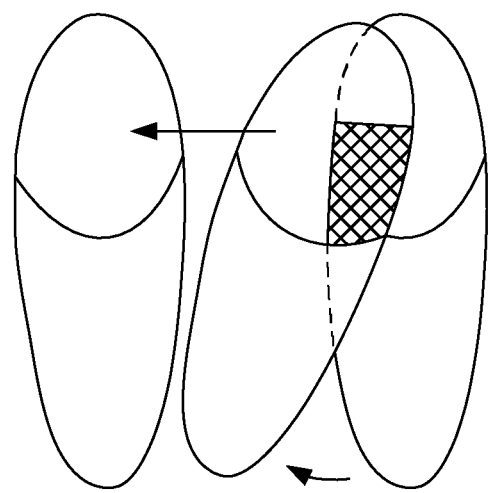
FIG. 9 shows non-linear movement of a tooth, according to an embodiment of the present invention.

A tooth movement may include moving a tooth linearly or non-linearly along a tooth movement path. Referring to FIG. 9, a non-linear movement path, e.g., to enhance the applied force in the mesio-cervical area is shown. Braces may be applied to the teeth such that more of a crown movement force might be elicited with braces alone. An aligner can be configured to further or additionally apply a root-moving force to the tooth and for application to the teeth in conjunction with the braces. The combination of the braces and the aligner, in such an instance, can be selected to provide a desired net movement (crown+root) to the tooth.

Designing a system for combined aligner and braces movement forces applied to the tooth may have the advantage of allowing a selection of brackets (e.g., bracket shapes, types, materials, ancillaries including hooks, brands, designs, etc., including banding) or bracket location/positioning on a tooth that might not otherwise be selected or available to a treating professional for delivery of the same tooth movement when only fixed braces alone are used. With regard to bracket positioning, for example, when using braces alone for treatment, a bracket is typically positioned on a tooth in a conventional manner at a prescribed position on the tooth (usually a middle crown point or the FA point if on the facial surface) to allow maximum accuracy and efficiency when eliciting the desired movement. Thus, alternate positioning is generally unavailable, thereby restricting the types of movements that might be accomplished, when using braces alone. When using a combined aligner and braces system, a different positioning of the bracket might be selected (e.g., bracket moved more toward the occlusal or gingival direction). A different type of bracket may also be selected (e.g., a more narrow bracket design) if a portion of the movement is planned to be accomplished through the aligner and not entirely by the wire. In one example, the positioning of one or more brackets might be modified so as to position the brackets lower on the tooth (or more gingivally), such that the braces are less visible or allow for improved aesthetics or in order to avoid the opposing teeth in the case of a deep bite, for improved comfort for the patient by positioning the bracket away from sensitive areas, for improved force or torque (e.g, rotational or tipping force), or otherwise accommodating a treatment preference of the practitioner or the patient. In another example, bracket positioning may be altered to accommodate combined aligner/braces treatment so as to allow for improved or altered tooth movements as described above.

Figure 10:
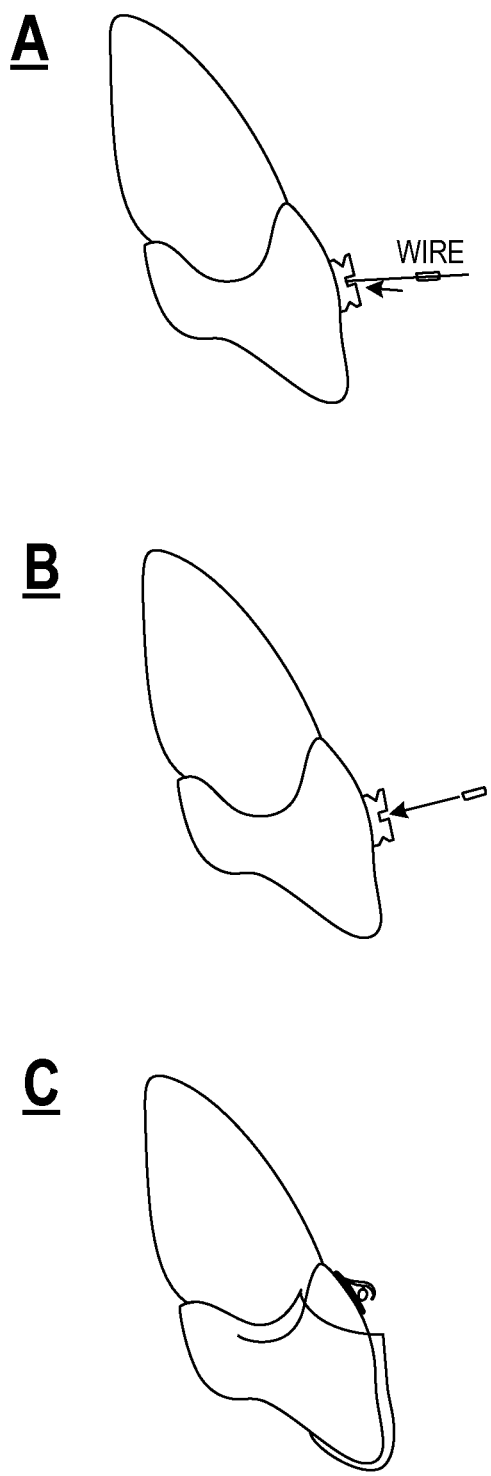
FIGS. 10A through 10C show positioning and selection of brackets and wires, according to an embodiment of the present invention.

FIGS. 10A through 10C shown positioning of brackets and wires, as well selecting alternate bracket positioning and bracket type/design, for use in combined aligner and braces systems and methods described herein. The position of the bracket on the tooth affects the position of the wire, and therefore affects the movement force applied to the tooth by the braces. Different movement foces and/or positioning of braces can be utilized when using a combination of current aligners and braces compared to use of braces alone. FIG. 10A shows bracket positioning on a tooth so as to accommodate normal facial axis (FA) point insertion position for a straight wire. FIG. 10B shows a modified position of the bracket on the tooth selected to accommodate use of a combined aligner and braces system. The bracket positioning shown in FIG. 10B is at a higher angle of insertion compared to positioning shown in FIG. 10A, and wire insertion is no longer the normal straight wire insertion. Such bracket positioning and wire insertion introduces different movement forces to the tooth (e.g., greater lingual inclination forces on the upper incisors than if inserted parallel to the occlusal plane), and an aligner can be designed to function in conjunction with such forces so as to elicit a desired tooth movement. FIG. 10C shows selection of a lower profile or wire clip type bracket with no inclination (i.e., a bracket that allows rotation and inclination dimension movement and all translations). The aligner includes a tooth-receiving cavity shaped such that the aligner edge is disposed either around or over at least some portion of the bracket to accommodate the bonded bracket while the aligner is being worn. Use of a combined aligner and braces system as described may further allow selection and use of different wires, such as round wire with a low profile bracket, where the aligner component reduces the minimum necessary force component required from braces in the orthodontic system.

Figure 11:
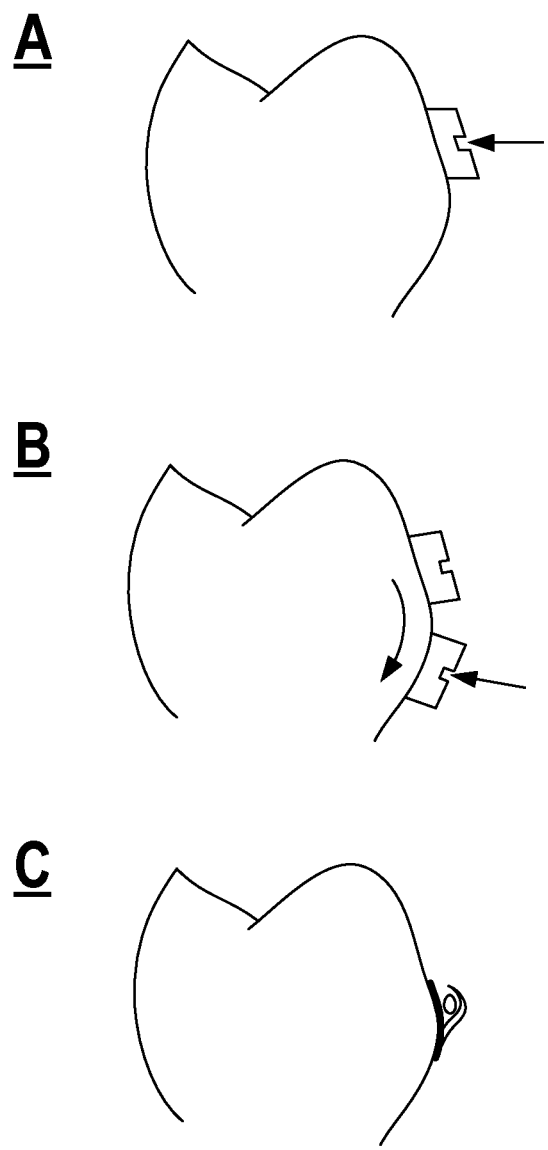
FIGS. 11A through 11C show positioning and selection of brackets and wires, according to an embodiment of the present invention.

Similarly, FIGS. 11A through 11C shown positioning of brackets on a tooth, including selecting alternate bracket positioning and bracket type/design, for use in combined aligner and braces systems and methods described herein. FIG. 11A show positioning of a bracket on a tooth (e.g., molar) for braces-only treatment, with FIG. 11B showing alternate or modified positioning of the bracket in a combined aligner and braces system. FIG. 11C shows selection of a lower profile or wire clip type bracket with no inclination (e.g., a 2-dimensional bracket), and bracket positioning on the tooth.

Thus, in some embodiments, designing a system for combined aligner and braces treatment may include selection or modification of a component of the braces, such as bracket or wire selection. With regard to brackets, brackets may be selected or shaped specifically to accommodate or even enhance/optimize treatment when used in combination with an aligner system. In other words, the bracket design is specific to address one or more particular weaknesses of the aligner design and the aligner design bolsters the weaknesses of the bracket design. For example, a lower incisor bracket can be designed such that it can be positioned more gingivally to avoid the lingual surfaces of the upper incisors during bite closure, but remain efficient for rotations because of the aligner component which engages the bracketed teeth in the incisal portion where rotational forces are more efficient to administer due to the greater mesial-distal width (in comparison to the incisor width near the gingiva). This removal of duplication efforts between the two components can allow for better appliance esthetics and patient comfort than using a combined off-the-shelf approach. A bracket may include a shape selected or designed to accommodate placement of an aligner on the patient's teeth and/or interaction between the bracket and the aligner. Brackets can be selected with one or more surfaces that contact or even engage a surface of an aligner. In one example, use of a combined aligner/braces system may allow selection of certain bracket shapes/designs that might not otherwise be available for a particular treatment or tooth movement. For example, certain low profile brackets, brackets having a simplified shape, flattened brackets, lingual brackets, so-called 2-dimensional brackets (such as those commercially available, e.g., from Forestadent, GmbH), may be selected for use in a combined aligner/braces system as described herein to accomplish tooth movements or treatments that may not otherwise be available or practical when using the same types of brackets in a braces treatment system alone. Bracket geometry may also be reduced to resemble an aligner attachment, such that it becomes a bracket-attachment hybrid (an attachment with a tube designed to engage an archwire for example). Additionally, particular brackets, such as those mentioned above, may be selected to reduce reduced contact or unwanted interference/contact between a bracket and an aligner surface.

Similar to bracket selection, other orthodontic device components (e.g., archwires, elastics) may be selected based on use of a combined aligner/braces system. For example, a particular archwire (e.g., size, shape, material properties, etc.) may be selected for use in a combined system where that archwire might otherwise be less desirable for a particular treatment or movement when using braces alone. For example, the doctor may be able to remain in a super-elastic nickel-titanium archwire for a longer period of time before switching to stainless steel, or remain in a more comfortable smaller dimension archwire longer before stepping up to a thicker wire.

In addition to some potential benefits alluded to above, a combined aligner and braces system as disclosed herein may advantageously reduce or limit contact between braces components, the teeth, and soft tissues (e.g., the tongue, cheeks, lips) of the patients mouth. For lingual bracket systems, for example, an aligner in a combined system may at least partially cover the brackets and/or reduce irritating contact between the patients tongue and one or more brackets positioned on the teeth. In another example, the sharp portions of the brackets such as the hooks may be covered by the aligner or even relegated completely to the design of the aligner itself (i.e, the hooks are in the aligner not in the bracket).

Figure 12:
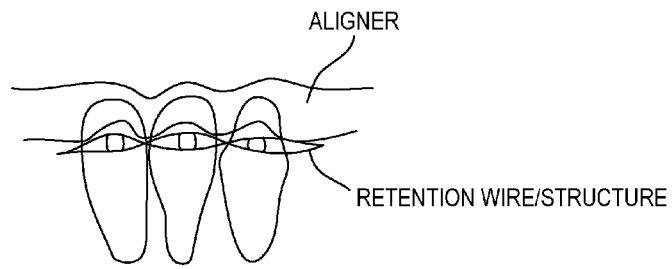
FIG. 12 shows an aligner shaped to accommodate a retention wire structure on a section of a patient's teeth.

As described herein, an aligner can be shaped to accommodate various components of an orthodontic braces structure, including brackets as well as wires and elastics. In traditional orthodontics, a wire retention structure around the braces may be implemented once teeth have moved to a desired position in order to retain the teeth in position for a selected time. In one embodiment, an aligner is shaped to accommodate, or even replace, a retention structure, such as a wire retention structure (e.g., ligature wire structure). FIG. 12 shows an aligner shaped to accommodate a retention wire structure on a section of a patient's teeth. In one embodiment, an aligner can be designed to hold the teeth in the desired position following prior movements, and can work in conjunction with a wire retention structure or may be designed to allow the aligner to provide the retention structure alone, thereby allowing removal of the wire retention structure—or replacement of the wire retention structure with an aligner shaped to retain teeth in the desired position. For example, an aligner can be shaped to receive the bracket-positioned teeth and hold the bracketed teeth firmly in place, preventing movement of the teeth or relapse. In such an example, the braces may be left on the teeth without the wire, in case additional tooth movement with a wire is required, but the wire is not needed with ligature wire (for hygiene benefits) because the aligner portion will hold the bracketed teeth in the desired position.

As described above, braces or bracketed teeth will span two or more teeth, and may include two or more bracketed teeth adjacent to each other, as well as one or more unbracketed teeth positioned between bracketed teeth. In some instances, braces may be affixed to a section of two or more teeth where the section includes one or more teeth not having braces/ brackets affixed thereto. Such an arrangement may be selected, for example, where one or more teeth within a section of teeth are positioned in a manner where positioning of a bracket is either undesirable or not practical/possible. This may be the case when restored surfaces such as composite, metal or porcelain are present, which can be difficult to bond brackets to, but tooth movement of the tooth/teeth in between is desired. Thus, in one embodiment, a system can include an aligner shaped to accommodate one or more teeth positioned between two braces or bracketed teeth. The aligner can be designed or shaped so as to elicit movement to said unbracketed tooth/teeth while accommodating movement to the adjacent bracketed teeth with a braces appliance. An example of a longer span in this situation would be the movement of anterior teeth restored with porcelain veneers where bonding brackets to the veneered teeth risks damage to the veneers upon removal of the braces.

Referring to FIG. 13A, a section of teeth is shown including at least one tooth positioned between two teeth having brackets attached thereto. In one example, movement of the middle tooth may be desired even though placement of a bracket on that tooth is impractical due to relative positioning of the teeth (e.g., severe crowding leading to a tooth being blocked from access for bracket bonding), desired movement that might be impeded by the thickness of a bonded bracket, or the like. FIG. 13B shows an aligner positioned on a patient's teeth, with a portion of the aligner receiving the teeth of the section. The aligner may be shaped to elicit movement of the middle tooth or unbracketed tooth as well as accommodate braces positioned on the adjacent teeth. Arrows show example movement or force vectors applied to teeth in the section. Movement of the teeth in one phase of treatment as shown may be followed by use of braces over the entire section of the teeth (e.g., once movement of the teeth has sufficiently occurred so as to permit the placement of a bracket on the middle tooth and/or the practical use of braces on all teeth in the section).

Figure 14:
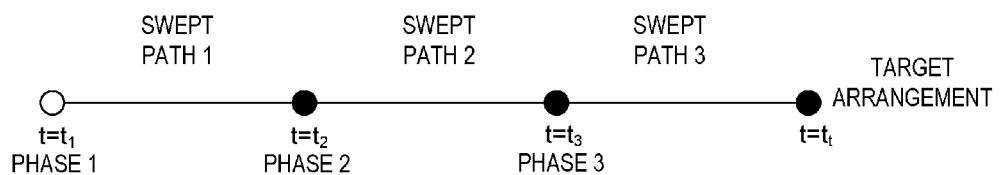
FIG. 14 illustrates a treatment line showing a plurality of phases of orthodontic treatment and a plurality of swept tooth paths, according to an embodiment of the present invention.

As indicated above, the aligners as described herein can be employed individually or as a component of an orthodontic treatment including a number of aligners, appliances, as well as a number of treatment stages or phases. The aligners can be applied to one arch or both. The increment of time in movement between any two positions may include an intermediate position which is a detour and not along the direct path towards the final, if the position is to move a tooth in a non-linear manner (i.e., with a deviation from the most direct path towards the final). Thus, as illustrated with reference to FIG. 14, orthodontic treatment may include a number of treatment stages of phases, and may include a number of different movement paths. A phase of treatment may include one or more aligners with a given movement path, such as a plurality of aligners including a particular movement path volume or geometry to accommodate movement of a bracketed tooth or teeth.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention. Any stated advantages herein will be recognized as non-limiting and/or optional advantages depending at least partially on the selected design or use according to structures and methods described herein.

What is claimed is:

1. A method of providing an orthodontic appliance for moving a patient's teeth, comprising:
   identifying a first position of one or more bracketed teeth;
   identifying a second position of the bracketed teeth according to a treatment plan;
   determining a tooth movement geometry based on a movement path of the bracketed teeth from the first position to the second position;
   fabricating an aligner comprising a first portion having teeth receiving cavities shaped to receive and resiliently position teeth, and a second portion having teeth receiving cavities shaped to receive bracketed teeth of the patient, the second portion shaped based on the movement path geometry and configured so as to accommodate movement of the patient's bracketed teeth between the first position and the second position of the treatment plan elicited by force from a bracket and wire orthodontic braces appliance worn by the patient, wherein the second portion accommodates movement of the patient's bracketed teeth relative to the second portion during movement between the first and second positions.

2. The method of claim 1, wherein identifying a position of a bracketed tooth comprises generating a digital model of a tooth having a bracket.

3. The method of claim 2, further comprising modifying a shape or position of a digital bracket on a digital tooth.

4. The method of claim 1, wherein the movement path comprises a volume defined by a tooth moving between a plurality of intermediate positions or tooth arrangements between the first position and the second position.

5. The method of claim 1, wherein the second portion comprises a bracket relief portion comprising a bubble, protrusion, envelope, or slot shaped portion.

6. The method of claim 5, wherein the relief portion is shaped to accommodate a bracket and wire such that the wire is disposed either entirely within the relief portion or at least partially outside the relief portion when the appliance is positioned on the patient's teeth.

7. The method of claim 1, wherein a tooth receiving cavity of the second portion is shaped to restrict at least one direction or path of movement of a received tooth during orthodontic treatment.

8. The method of claim 1, wherein a tooth receiving cavity of the second portion is shaped to restrict extrusion during tooth rotation or translation.

9. The method of claim 1, wherein a tooth receiving cavity of the second portion comprises an active portion that contacts a received tooth so as to apply a force to the tooth.

10. The method of claim 1, wherein the second portion is shaped to accommodate a plurality of bracketed teeth.

11. The method of claim 1, wherein the second portion is shaped to accommodate an unbracketed tooth disposed between two bracketed teeth.

12. The method of claim 1, wherein the first position of the one or more bracketed teeth comprises a position of the patient's teeth occurring prior to the patient's current teeth positions.

13. A system for orthodontic movement of a patient's teeth according to a treatment plan, comprising:
   an orthodontic braces appliances comprising brackets for positioning on the patient's teeth; and
   a shell-type aligner comprising a first portion having teeth receiving cavities having geometries to receive the patient's unbracketed teeth, and a second portion having a tooth receiving cavity shaped to receive a bracketed tooth of the patient, the second portion shaped based on a movement path geometry accommodating movement of the patient's bracketed tooth between a first tooth position and a second tooth position as at least partially elicited by force from the orthodontic braces appliance worn by the patient, the first tooth position corresponding to a position of the bracketed tooth in the treatment plan and the second tooth position corresponding to a subsequent position of the bracketed tooth in the treatment plan, wherein the second portion accommodates movement of the patient's bracketed tooth relative to the second portion during the movement between the first and second tooth positions.

14. The system of claim 13, wherein the movement path geometry comprises a volume defined by the bracketed tooth moving between a plurality of intermediate positions between the first and second tooth positions.

15. The system of claim 13, wherein the tooth receiving cavity of the second portion comprises a bracket relief portion.

16. The system of claim 13, wherein the tooth receiving cavity of the second portion defines a bracket insertion channel shaped to receive a bracket as the shell-type aligner is at least one of positioned or removed from the patient's teeth.

17. The system of claim 15, wherein the bracket relief portion comprises a bubble, protrusion, envelope, or slot shaped portion.

18. The system of claim 15, wherein the bracket relief portion is shaped to accommodate a bracket and a wire.

19. The system of claim 17, wherein the bracket relief portion is shaped such that the wire is disposed at least partially outside the bracket relief portion when the shell-type aligner is positioned on the patient's teeth.

20. The system of claim 13, wherein the tooth receiving cavity of the second portion is shaped to restrict at least one direction or path of movement of the bracketed tooth during orthodontic treatment.

21. The system of claim 20, wherein the tooth receiving cavity of the second portion is shaped to restrict extrusion during tooth rotation or translation.

22. The system of claim 13, wherein the tooth receiving cavity of the second portion comprises an active portion that contacts the bracketed tooth so as to apply a force to the bracketed tooth.

23. The system of claim 22, wherein the active portion is shaped so as to contact and apply a force to the bracketed tooth during only a portion of the movement of the bracketed tooth between the first and second tooth positions.

24. The system of claim 22, wherein the active portion is shaped to provide a leverage contact surface for application of a force applied by the orthodontic braces appliance.

25. The system of claim 13, wherein the second portion is shaped to accommodate the orthodontic braces appliance comprising a low profile, wire clip, or two-dimensional bracket.

26. The system of claim 13, wherein the second portion is shaped to accommodate the orthodontic braces appliance comprising a retention wire structure.

27. The system of claim 13, wherein the second portion is shaped to accommodate a plurality of bracketed teeth.

28. The system of claim 27, wherein the second portion is shaped to accommodate an unbracketed tooth disposed between two bracketed teeth.

* * * * *